United States Patent [19]

Robbins

[11] Patent Number: 4,945,254

[45] Date of Patent: Jul. 31, 1990

[54] METHOD AND APPARATUS FOR MONITORING SURFACE LAYER GROWTH

[75] Inventor: David J. Robbins, Malvern, Great Britain

[73] Assignee: The Secretary of State for Defence in Her Britannic Majesty's Government for the United Kingdom of Great Britain and Northern Ireland, London, England

[21] Appl. No.: 276,195

[22] Filed: Nov. 21, 1988

[30] Foreign Application Priority Data

Mar. 19, 1986 [GB] United Kingdom ............... 8606748
Mar. 17, 1987 [WP] PCT Int'l Appl. .... PCT/GB87/00187

[51] Int. Cl.$^5$ ............................................. G01N 21/86
[52] U.S. Cl. ..................................... 250/571; 356/445
[58] Field of Search ............... 356/446, 447, 448, 445; 250/571, 572

[56] References Cited

U.S. PATENT DOCUMENTS

| | | | |
|---|---|---|---|
| 2,892,490 | 6/1959 | Shakesby | 157/1.5 |
| 3,492,491 | 1/1970 | Beeh | 250/222 |
| 3,700,903 | 10/1972 | Adler | 356/447 |
| 3,853,093 | 12/1974 | Baker et al. | 118/8 |
| 4,039,370 | 8/1977 | Kleinknecht | 250/571 |
| 4,091,060 | 3/1978 | Carter et al. | 264/40.1 |
| 4,142,107 | 2/1979 | Harakis | 250/571 |
| 4,198,261 | 4/1980 | Busta et al. | 156/626 |
| 4,201,474 | 5/1980 | Holl | 356/445 |
| 4,332,833 | 6/1982 | Aspnes et al. | 427/8 |
| 4,420,826 | 12/1983 | Marshall, Jr. et al. | 367/167 |

FOREIGN PATENT DOCUMENTS

0061237 9/1982 European Pat. Off. .
731865 6/1955 United Kingdom .
1488049 10/1977 United Kingdom .

Primary Examiner—David C. Nelms
Assistant Examiner—Sherrie Hsia
Attorney, Agent, or Firm—Nixon & Vanderhye

[57] ABSTRACT

A method of monitoring surface layer growth using light scattered off a surface illuminated e.g. by a laser. A small area of a surface of a substrate is illuminated and the light scattered in a non-specular direction is detected during cleaning and subsequent layer growth. The amount of light scattered varies strongly with surface characteristics and gives clear indication of the end of oxide removal, initiation of nucleation and quality of growing layers. The monitoring is used during e.g. chemical vapor deposition, or e.g. molecular beam epitaxy growth processes.

23 Claims, 6 Drawing Sheets

METHOD AND APPARATUS FOR MONITORING SURFACE LAYER GROWTH

BACKGROUND OF THE INVENTION

Many device manufacturing processes involve cleaning, preparation and depositing thin layers on a substrate. The degree of perfection of a thin film on a substrate is important in many and diverse applications. Examples are semiconductor layers, epitaxial, polycrystalline or amorphous, insulating layers, thin film coatings on optical components and on optical or magnetic memory devices, etching of surfaces, and preparation of non-specular surfaces e.g. solar converters.

Some of the factors determining the quality of a thin film are the perfection and the cleanliness of the substrate surface. The same is true for deposition of subsequent films. It is not easy to clean say a layer of silicon oxide off a silicon substrate without either incompletely cleaning the surface or removing material from the substrate surface. Both may degrade the interface between substrate and grown layers.

Various systems are now in use for growing layers. For example chemical vapour deposition (CVD), and molecular beam epitaxy (MBE). These processes are carried out in closed chambers that can be thoroughly cleaned. There remains the problem of knowing what is happening at the surface of a substrate in the closed chamber.

Use of scattered light to monitor growing interfaces is known from O. N. Mesquita et al, Physical Review B, Vol. 29 No. 5, 1 Mar. 1984, pages 2846–2849; and H. Durig et al, Physical Review A, Vol. 30 No. 2, Aug. 1984, pages 946–959. These describe directing light through a crystal to the crystal-liquid interface in a zone refining cylinder. Reflected light provides information about crystalline growth at the interface.

Such prior art provides no information on the cleaning and subsequent growth of epitaxial layers on a flat slice of semiconductor material.

Surface statistics, roughness, etc., can be calculated from scattered light. This is described in Optical Engineering, Jul./Aug. 1984, Vol. 23 No. 4, J. C. Stover et al, pages 406–412; Applied Optics, 15 Oct. 1984, Vol. 23 No. 20, P. Roche & E. Pelletier, pages 3561–3566; S.P.I.E. Vol. 511, Stray Radiation IV 1984, R. M. Silva et al, Pages 38–43.

Specularly reflected light has been used in the growth of coating layers. See for example U.S. Pat. No. 3,892,490, G.B. Patent No. 731,865, European Patent No. A.2, 0,150,945.

The above problem is solved according to this invention by directing a beam of light onto the surface of a substrate and detecting light scattered off the substrate in a non-specular reflection direction. Changes in the intensity of detected light are then used to change process parameters, e.g. change from a cleaning step to a layer growth step.

According to this invention a method of monitoring surface conditions on a surface of a substrate being processed includes the steps of:
directing a beam of light onto at least one small area of the surface being monitored;
detecting light scattered from said small area in at least one non-specular reflection direction;
changing the process parameters in response to detected changes on the surface.

The processing of the surface may be a cleaning, a removal of oxide or other compound, a deposition of layers of materials the same or different from the original, substrate, surface. These layers may be deposited by chemical vapour deposition (CVD), metal organic chemical vapour deposition (MOCVD), molecular beam epitaxy (MBE), etc.

The change in process parameters may be a change from a cleaning step to a growth of layers, or a change from growing layers of different materials or cessation of growth at a specified end point.

SUMMARY OF THE INVENTION

Preferably the processing is carried out in a vessel capable of withstanding high or very low pressures. This enables the vessel and contents to be thoroughly cleaned prior to and during processing.

According to this invention apparatus for monitoring surface conditions of a substrate includes:
a closed vessel capable of holding a substrate to be processed,
means for cleaning or otherwise preparing a surface of the substrate,
means for depositing a layer of material on the cleaned surface,
characterised by:
means for directing light onto at least one small area of the surface less than the total area of the surface,
means for detecting light scattered from the small area in at least one non-specular reflection direction,
means for changing the cleaning or layer growth parameters in response to detected changes or scattered light.

Preferably the vessel is a pressure vessel and or a vacuum tight vessel and contains different sections with air locks to allow loading and discharging of contents without contaminating of the cleaning and growth section.

An argon ion laser emitting at 488 nm may be used for the light source. The light source may be operated continuously, or pulsed ON and OFF. Alternatively white light or other non-laser light sources may be used. The light may be plane polarised and its polarisation axis may be rotated relative to the surface being monitored. Measurements at different angles of polarisation are then made. The detector may be a photon counting photomultiplier tube with a 488 nm bandpass filter.

The amount of light scattered in a non-specular direction has been found to be unexpectedly high. It is very sensitive to surface changes on a nanometer scale that occur e.g. during cleaning and deposition of silicon. In some cases the surface features generated by cleaning or deposition are directional and or periodic. In this case the intensity of scattered light varies strongly with angle of incidence and direction of detection. More detailed information on topography can therefore be obtained from measurements in more than one direction. Also the intensity of scattering in a given direction is wavelength dependent. Further information is obtained from measurements at different wavelengths.

Non-specular light may be detected both on reflection from a surface or just below the surface, and after transmission through a substrate. The light may be scanned over the surface of one or more substrates to form a map of the or each substrate.

Principal uses of the above method are

1. To display in real time changes in surface topography during preparation and cleaning of substrate, and during later deposition.

2. To control changes in process parameters in response to measured surface changes, in order to optimise cleaning or growth conditions.

3. To monitor effects of changes in process parameters, to ensure they comply with specified limits.

4. To indicate specified end point during deposition (or etching) sequence.

5. To 'map' substrate surface if scanning optics or a moving substrate system is used, to monitor uniformity in processing.

6. To indicate a particular growth mode e.g. step arrays, solid phase epitaxy, surface segregation.

7. To indicate the existance of defects in a growing layer.

BRIEF DESCRIPTION OF THE DRAWINGS

The invention will now be described, by way of example only, with reference to the accompanying drawings of which.

DETAILED DESCRIPTION OF PREFERRED EMBODIMENTS

Figure 1:
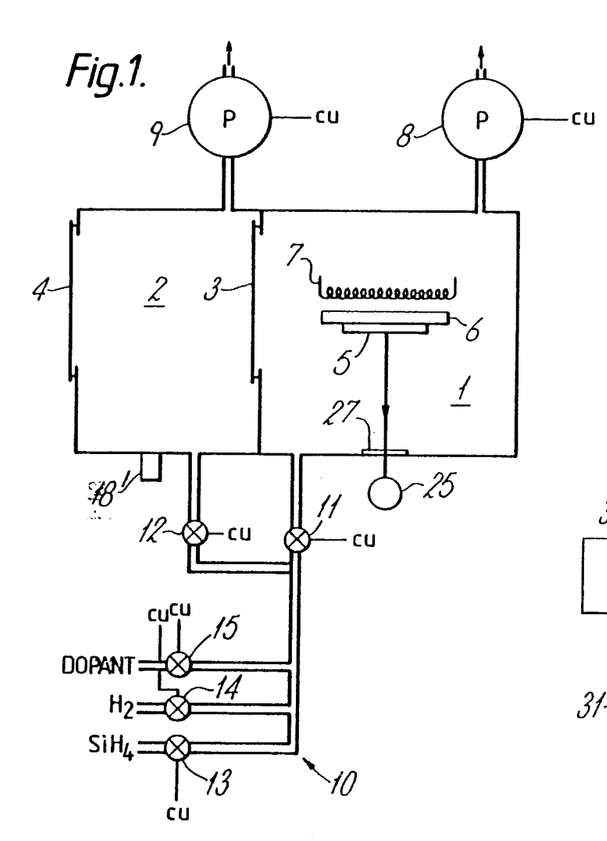
FIGS. 1, 2 are schematic side and end views of a pressure or vacumn chamber for growing thin layers on a substrate.
Figure 2:
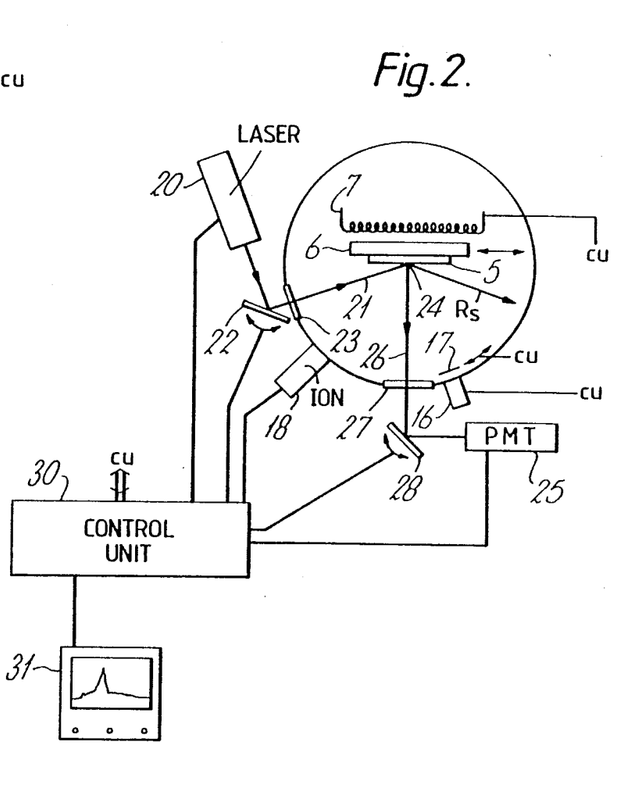

The apparatus shown somewhat schematically in FIGS. 1, 2 is for cleaning substrates and growing layers thereon. The apparatus comprises a main growth chamber 1 capable of withstanding a high pressure or a very low pressure. Fixed to the growth chamber 1 is a loading chamber 2 which comunicates with the inside of the growth chamber 1 through an entry lock 3. An entry lock 4 on the loading chamber 2 allows loading of substrates 5. Inside the growth chamber 1 is a substrate holder 6 capable of movement to move a substrate between chambers. A heater 7 is arranged to heat the substrate 5 to the required temperature. Pumps 8, 9 evacuate the chambers 1, 2 as required. An inlet manifold 10 supplies various gases to the growth chamber 1 through a valve 11 and to the loading chamber 2 through a valve 12. As shown the manifold 10 receives three gas supplies of e.g. silane, hydrogen, and dopant, through valves 13, 14, 15. Knudson ovens 16 (one only shown) supply their contents onto the substrate 5 as allowed by associated shutters 17. An ion gun 18 is arranged to irradiate the substrate 5 as needed.

An argon ion laser 20 emitting about 10 mW at 488 nm is mounted to direct its light output 21 via scanning optics 22 and a window 23 onto a small area 24 on the substrate 5. Laser light 21 will reflect in a specular manner as indicated by line Rs but this specular reflection is not used. Instead a detector 25 is mounted above the substrate 5 to receive light 26 via a window 27 scattered in the plane of the laser light 21 in a non-specular direction. Other angles and planes may be chosen instead of or in addition to that shown. The detector 25 may be a photon counting photomultiplier tube with an 488 nm bandpass filter, suitable collecting lens and aperture. Scanning optics 28 allow the detector 25 to scan the surface of the substrate 5 and may be linked to that of the laser scanning optics 22.

A control unit 30, e.g. a computer, is linked to each valve 13, 14, and 15, pump 8, 9, oven 16, gun 18, heater 7, optics 22, 28, laser 20 and detector 25 to control growth of layers as described below. Additionally a cathode ray tube (CRT) 31 or graph plotter may be used to provide a visual display of the detector output and allow manual control of the apparatus in cleaning and growing layers. An additional laser (not shown) may be used as a second light source to modulate growth i.e. photo assisted processing.

Specularly reflected light R, may be detected and used in a feedback loop to stabilise the laser 20 output power. Additionally specular reflected light may also be detected and used to allow for unwanted coating of windows 23, etc. Such a coating may build up from unwanted depositions of materials within the chamber 1. This compensation for window coating may employ light from the laser 20 or a further laser directing light through the window 27. In this latter case the specular light would also be received through this same window 27.

The apparatus of FIGS. 1, 2 can be used to process silicon wafer substrates for devices at a lower temperature e.g. 850° C. instead of the more usual 1,000° C. Principal stages in the reduced temperature silicon epitaxy are:

(1) Substrate pre-clean, e.g. the known RCA clean, outside the chambers;

(2) Substrate surface oxide removal in the growth chamber 1 or in chamber 2 e.g. sputter clean;

(3) deposition and/or doping on the substrate in the growth chamber 1, using CVD or MBE techniques.

Example of growing epitaxy layers of silicon using CVD techniques.

Step 1.

Clean a silicon wafer using R.C.A. technique or rinsing in aqueous H.F. followed by rinsing in deionised water and drying.

Cleaning with the R.C.A. technique leaves a layer of thermally labile oxide that is relatively easy to remove.

Step 2.

Load cleaned wafer into loading chamber and reduce pressure to $\sim 10^{-7}$ mB.

Step 3.

Load wafer into evacuated growth chamber and flow H2 whilst operating pump 8 to maintain pressure at about 1.33 mB (1 Torr.).

Step 4.

Initiate scatter measurements by illuminating an area of about 0.1 cm$^2$ by the laser and detecting scattered light.

Step 5.

Heat wafer with heater 7 to 850° C. at a slow rate. The point at which the wafer substrate reaches 850° C. is indicated at O on FIG. 3. This indicates the start of oxide desorption at the area of laser illumination.

Heating continues for about 5–15 minutes whilst the oxide continues to be desorbed and the light scattering increases due to increasing roughness of the oxide and substrate surface. Point A on FIG. 3 indicates the break up of the oxide layer. If the cleaning step is continued the surface roughness increases to point B. After point B the temperature of the wafer has been reduced to about 825° C. and the surface roughness is seen to remain resonably steady.

Figure 3:
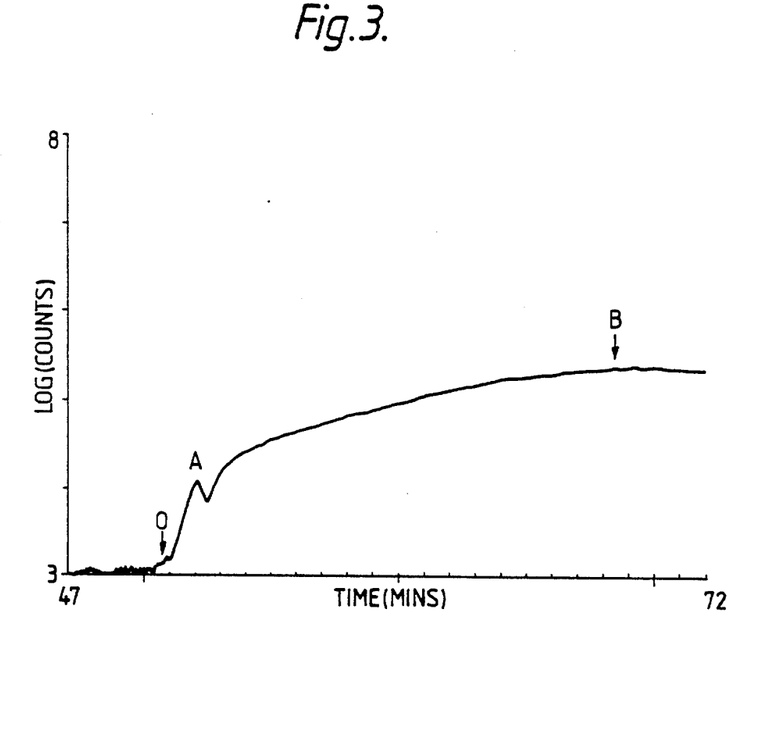
FIG. 3 is a graph showing scattered light against time of a silicon substrate being cleaned of an oxide layer.

If the oxide layer is a native oxide then a higher temperature is needed to move it in the same time. A native oxide can also be removed by reactive etching using an element which itself produces a volatile oxide. A convenient reaction in silicon epitaxy uses silicon atoms:

$$Si + SiO_2 \xrightarrow{800-850° C.} 2SiO \uparrow$$

The silicon atoms can be generated from thermal decomposition of a low $SiH_4$ flux. In an M.B.E. process the atoms could be produced from an e-beam hearth.

Figure 4A:
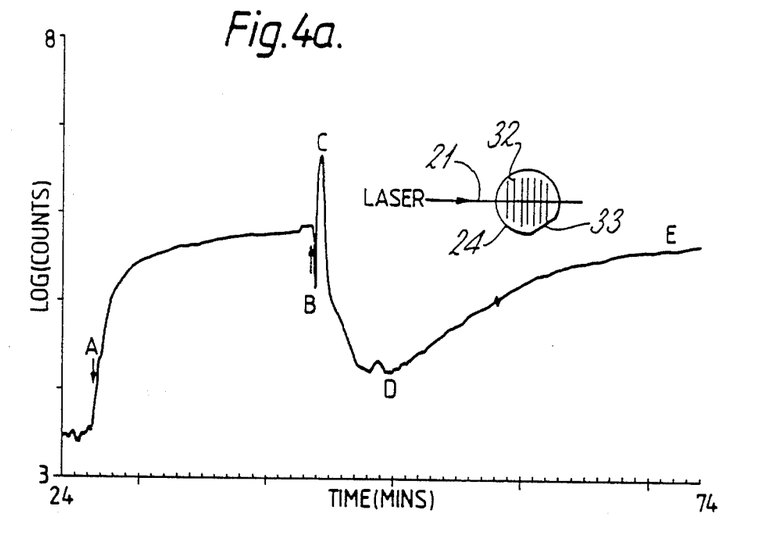
FIGS. 4(a), (b) are graphs showing growth of a silicon layer using light measurements from two different directions.

A similar graph is obtained for other wafers as shown in FIGS. 4(a), (b) and 5(a), (b). Break up of oxide is observed at A and roughness increases towards B.

Step 6.

To grow a layer of silicon on the cleaned surface the gas silane ($SiH_4$) is admitted at a typical rate of 1–100 sccm (standard cubic centimeter per minute) in excess $H_2$ with the pressure remaining at 1.33 mB.

Figure 4B:
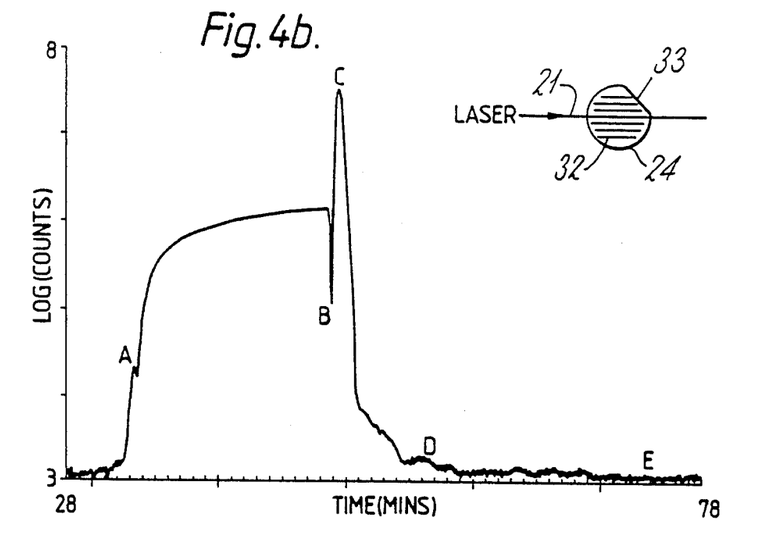

The effects of silane are observed at point B in FIG. 4(a), (b), the drop in scattered light is considered to be a smoothing action of growing silicon. A short time later, at point C, nucleation has started and the scattered light reaches a high value. Thereafter the growing surface becomes smoother and scattered light reduces to point D. FIGS. 4(a) and 4(b) are for similar wafers but measured in orthogonal directions.

For semiconductor epitaxy the preferred growth mode is by two-dimensional propagation of lattice steps. This growth mode favours atomically-flat interfaces and uniform dopant incorporation, both very important for e.g. superlattices. For a crystal plane only slightly off the <100> plane the substrate surface will be a series of steps typically about 1,000 Å wide and about 5 Å high. Under particular growth conditions periodic linear arrays of steps can be produced on the growing surface.

Nomarski interference microscopy and surface profiling indicate these step arrays to have a peak valley depth of about 3 nm and a perioed of about 1 um. The formation and propagation of such step arrays is easily detected as shown in FIGS. 4(a) and 4(b). In FIG. 4(a) the peaks and valleys 32 are normal to the direction of the laser light 21. In FIG. 4(b) the peaks and valleys 32 are parallel to the laser light 21. This is indicated at the top right hand corner of the graphs. A flat 33 on the circle indicates the <110> crystalline direction.

As seen in FIG. 4(a) the growing surface becomes smoother after nucleation at point C until a low point is reached at D. Thereafter the surface scatter increases up to point E as the effects of peaks and valleys become more pronounced. This results from strong diffraction of the laser light in the direction of the detector by the periodic step array. In FIG. 4(b) the growing surface after nucleation at C becomes smoother up to point D and the scatter remains approximately the same as the layer continues to grow out to point E. For this orientation the periodic step arrays do not diffract in the direction of the detector. Thus for some applications it is necessary to be able to rotate the direction of the laser light 21 relative to the growing layer to obtain maximum information.

Figure 5A:
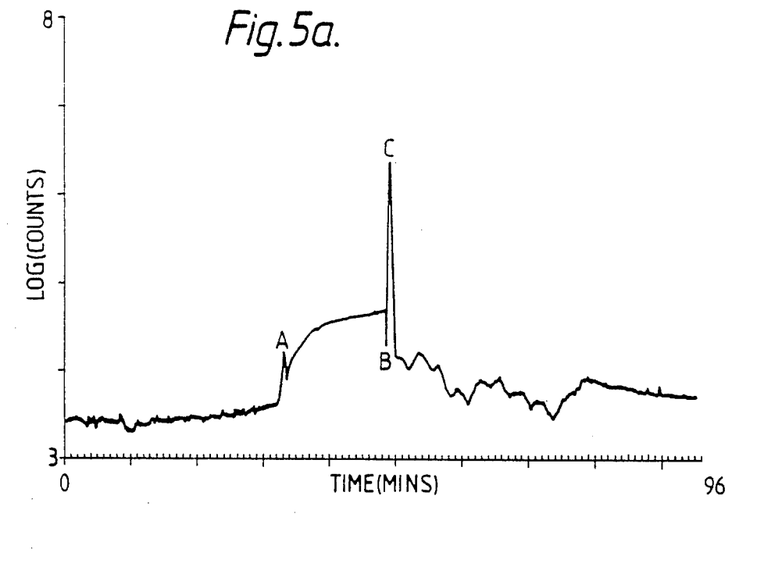
FIGS. 5(a), (b) respectively show growth of a good and a poor quality layer of silicon.
Figure 5B:
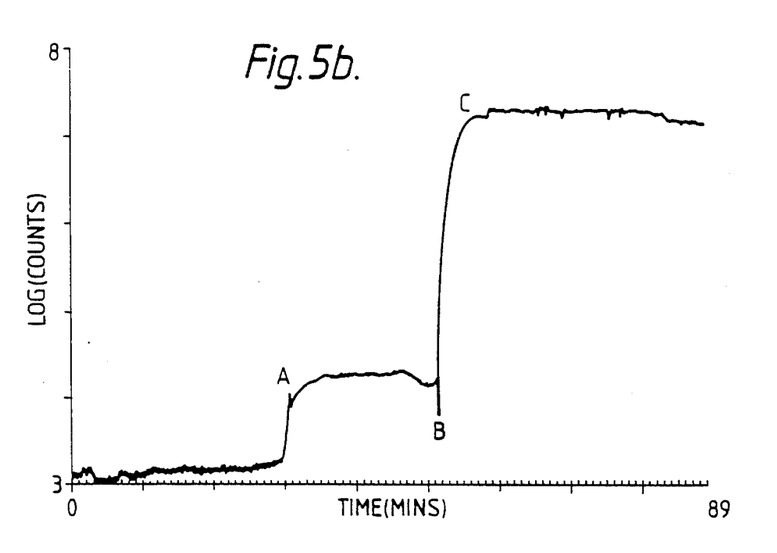
Figure 5C:
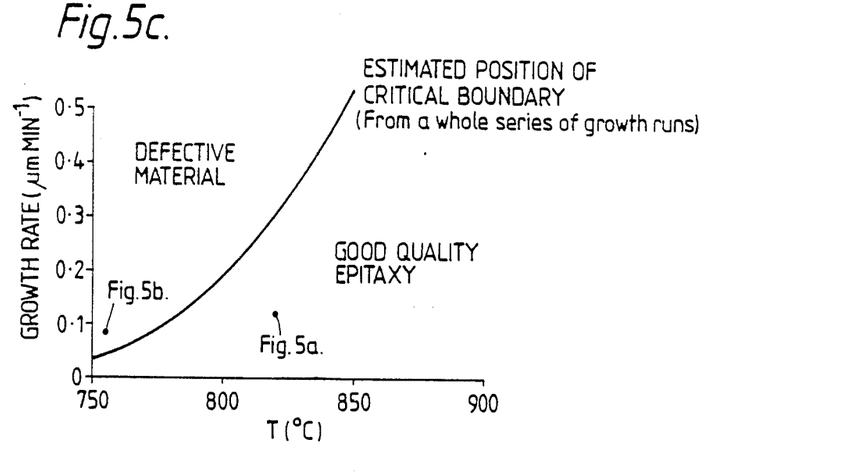
FIG. 5(c) shows the approximate boundary between good quality and poor quality crystalline material for different growth rates with temperature.

A further feature readily observed during growth is the quality of growing layer. This is seen in FIGS. 5(a), (b) taken with FIG. 5(c). FIG. 5(c) shows growth rate plotted against growth temperature derived from experiments on C.V.D. using $SiH_4$. A boundary line is seen that divides good quality epitaxial growth from poor quality high defect level growth. The sample shown by FIG. 5(a) was cleaned at 860° C. and grown at 820° C. using a silane flow of 10 sccm and $H_2$ flow of 400 sccm. In FIG. 5(a) the removal of oxide is seen at point A and the introduction of silane at B. Nucleation at C was followed by growth with continued reduction in measured scattered light.

The sample shown by FIG. 5(b) was cleaned at 860° C. and grown at 755° C. using a silane flow of 10 sccm and $H_2$ flow of 400 sccm. After introduction of silane at point B nucleation occurs at C. Thereafter the growing surface remains at a high scatter level due to the many surface defects. Thus the quality of growing surface can be measured in real time and any corrections made as they become necessary.

Step 7.

Stop silane flow when the desired depth of silicon has been grown.

Step 8.

Different gases may be flowed into the growth chamber to grow different layers. For example silane plus a dopant such as diborane may be used to grow a doped layer. The growth of this and any subsequent layers is monitored by scattered light as above. This technique is likely to be very useful for complex structures, e.g. superlattices, where many process changes have to be made, and monitored.

Step 9.

Remove wafer from chambers.

Example of growing layer of silicon on silicon wafer using MBE techniques.

Step 1.

Load wafer of silicon into loading chamber, reduce pressure to $\sim 10^{-7}$ mB to degass wafer and chamber.

Step 2.

Transfer wafer into growth chamber 1 held at a vacuum of $\sim 10^{-10}$ mB by the pump 8.

Step 3.

Illuminate a small area of wafer with laser light and measure the non-specular scattered light.

Step 4.

Figure 6:
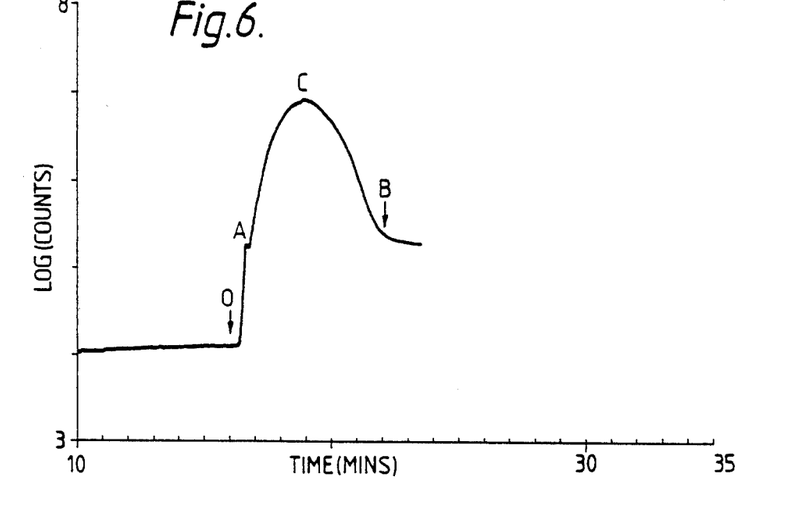
FIGS. 6, 7, 8 are graphs showing growth of silicon layers using MBE techniques.
Figure 7:
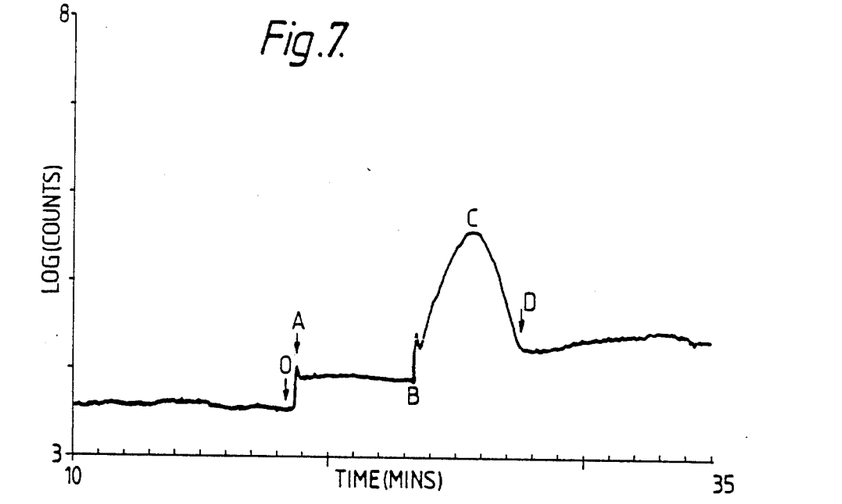
Figure 8:
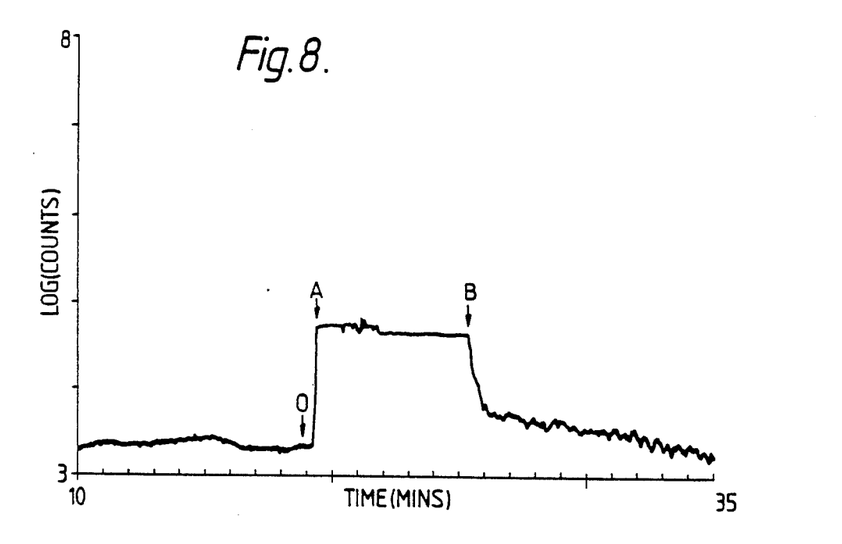

Slowly raise the temperature of the wafer to 850° C. with the heater 7. FIGS. 6, 7, 8 show wafers being processed by MBE. Up to point 0 the scattered light remains reasonably constant as the wafer heats up.

Step 5.

Open the shutter 17 to allow silicon from the Knudson oven or other Si source to flow onto the wafer. A typical rate is about $5 \times 10^{14}$ atoms per $cm^2$ per sec. The point at which the Si shutter opens is indicated at point 0. Thereafter there is a short induction period during which the native oxide is etched according to the reaction $$Si \text{ (beam)} + SiO_2 \xrightarrow{(850° C.)} 2SiO \uparrow$$

As the last of the oxide is being removed there is an increase in light scattering. At point A there is a peak in the scattered light analogous to the peak A in the FIGS. 4. Thereafter the scattering increases to point C where nucleation occurs and layer growth commences. This peak appears much wider than those in CVD growth due primarily to the low growth rate in MBE deposition; typically about 1 Å per sec.

Step 6.

Close Si shutter after the required amount of Si has been grown. Point B on FIG. 6 indicates closing of this shutter.

FIG. 7 indicates a slightly different procedure from the above. As before the Si shutter is opened at point 0 and scattering increases. At point A the shutter 17 is closed. The light scattered continues to remain reasonably constant until the shutter 17 is again opened at point B still at 850° C. The further step in the curve perhaps indicates that oxide removal was not initially complete. After point B the scattering increases due to nucleation to point C. Growth follows until at point D the Si shutter 17 is closed. Scattering remains reasonably constant afterwards.

FIG. 8 indicates yet another different procedure. As before a wafer is heated to 850° C. and the Si shutter opened at point 0. Scattered light increases up to point A when the shutter is closed. Between points A and B the wafer temperature is lowered to 825° C. whilst the scattered light remains constant. The Si shutter is opened at point B and nucleation and layer growth commences. The scattered light is at a lower level than before. Subsequent measurements indicate this signifies lower defect levels in the grown layer. Therefore the scattering at point A could be taken as signal to close the Si shutter after cleaning to allow a reduction in substrate temperature for optimum nucleation and growth.

Using the apparatus with light scattering measurements as described above other phenomena can be detected as follows:

1. Desorption of surface films from Si wafers at about 100° C. This typically shows as a decrease in scatter intensity.

2. Re-ordering of the amorphised surface of an Si wafer produce after oxide removal by ion bombardment. If Ne- ions at about 6 kV are used for sputtering the surface re-orders at about 620° C. Small peaks in scattering associated with this change have been detected.

3. Increases in scattering have been observed when beams of MBE dopants, e.g. Ga, Sb atoms, impinge on the Si surface. These atoms tend to accumulate on the Si surface. Sub-monolayer coverage produces large changes in scattering.

4. Emergence of the crystallisation front in solid phase epitaxy of Si. If Si is deposited on a clean wafer at low temperature, say <300° C., it forms an amorphous layer. Raising the temperature to, say, >600° C. will cause the amorphous layer to crystallise from the original interface. When that recrystallisation front reaches the layer surface there is a large change in scattering.

5. Accumulation of particulates on a surface. These tend to produce step increases in scattering intensity, and are very detrimental to layer quality.

6. After nucleation has started scattering levels are observed that are periodic in time, e.g. periods of 10 secs. These are related to growth rate and may be used to monitor thickness. For example by counting a predetermined number of periods and stopping growth or changing to a different material.

In general the light scattering technique will be most sensitive when the scatterers on the surface have some dimension comparable with the wavelength. In the cases described above, where the roughness in the direction normal to the wafer is on the nanometer or atomic scale, strong scattering will require the lateral dimensions of the surface roughness to be much larger, e.g. 0.1 to 1 μm when using visible light. In the case where a growing layer is transparent to light it is possible to obtain information at the substrate/layer interface.

Using the changes in scattering shown in the FIGS. 3 to 8 the control unit 30 can be programmed to change the settings or operation of valves or Knudson ovens etc., to clean and grow multiple layers automatically. This is especially useful when growing super lattice structure with very thin multiple layers of different materials. It is also useful for V.L.S.I. devices where many very thin layers are needed.

I claim:

1. A method of monitoring surface conditions on a surface of a subtrate being processed including the steps of:
    directing a beam of light onto at least one portion of an area of the surface being monitored;
    detecting light scattered from said at least one portion of an area in at least one non-specular reflection direction;
    changing the process parameters in response to detected changes on said at least one portion of said area of said surface.

2. The method of claim 1 further including the initial step of mounting the substrate in a closed vessel.

3. The method of claim 1 further including the step of maintaining the inside of the vessel at a reduced pressure while gas is flowed over the substrate.

4. The method of claim 1 wherein said changing step includes changing the substrate temperature in response to changes in the detected light.

5. The method of claim 1 wherein said changing step inlcudes controlling a supply of material for coating the substrate.

6. The method of claim 3 wherein said gas contains a gas of material to be grown on said substrate surface.

7. The method of claim 1 wherein said scattered light is independently detected from a plurality of non-specular directions.

8. The method of claim 1 wherein said beam of light is a beam of polarised light.

9. The method of claim 8 wherein said beam of polarised light has a polarisation and said polarisation may be varied.

10. The method of claim 1 wherein said directing step includes scanning said beam of light across said substrate surface.

11. The method of claim 1 wherein said directing step includes directing a continuous beam of light.

12. The method of claim 1 wherein said directing step includes directing a pulsed beam of light.

13. The method of claim 1 further including the step of detecting intensity of incident reflected light and in response to said intensity controlling illumination on the substrate.

14. The method of claim 1 wherein different wavelengths of light are used to illuminate said portion of area of substrate.

15. Apparatus for monitoring surface conditions of a substrate including:
   means for cleaning or otherwise preparing a surface of the substrate;
   means for depositing a layer of material on the cleaned surface;
   means for directing light onto at least one portion of an area of the surface;
   means for detecting light scattered from said at least one portion of an area in at least one non-sspecular reflection direction; and
   means for changing one of cleaning and layer growth parameters in response to detected changes of scattered light.

16. Apparatus according to claim 15 including a closed vessel capable of holding said substrate and further including a laser for illuminating said area of substrate.

17. Apparatus according to claim 16 including means for scanning the laser light across surface of the substrate.

18. Apparatus according to claim 16 including means for flowing gases through the closed vessel, and for removing exhaust products from the closed vessel.

19. Apparatus according to claim 18 wherein the means for changing includes means for controlling the supply of gases through the chamber.

20. Apparatus according to claim 15 wherein the means for changing includes means for controlling the substrate temperature.

21. Apparatus according to claim 15 including means for detecting specularly reflected light from the substrate and said means for directing is responsive to said means for detecting specularly reflected light and further includes means for controlling the laser to stabilise its light output power.

22. Apparatus according to claim 15 including means for detecting non-specular reflected light in a plurality of different directions.

23. Apparatus according to claim 15 wherein said means for detecting light includes a photomultiplier tube.

* * * * *